(12) United States Patent
Bealka et al.

(10) Patent No.: US 8,698,006 B2
(45) Date of Patent: Apr. 15, 2014

(54) CO-FIRED METAL AND CERAMIC COMPOSITE FEEDTHROUGH ASSEMBLIES FOR USE AT LEAST IN IMPLANTABLE MEDICAL DEVICES AND METHODS FOR MAKING THE SAME

(75) Inventors: David Joseph Bealka, East Freetown, MA (US); Christien Matthew Vaillancourt, New Bedford, MA (US); Fred Michael Kimock, Macungie, PA (US); Emma Claire Gill, Mattapoisett, MA (US)

(73) Assignee: Morgan Advanced Ceramics, Inc., Hawyard, CA (US)

( * ) Notice: Subject to any disclaimer, the term of this patent is extended or adjusted under 35 U.S.C. 154(b) by 434 days.

(21) Appl. No.: 12/802,323

(22) Filed: Jun. 4, 2010

(65) Prior Publication Data

US 2011/0000699 A1  Jan. 6, 2011

Related U.S. Application Data

(60) Provisional application No. 61/184,076, filed on Jun. 4, 2009.

(51) Int. Cl.
| | |
|---|---|
| *H05K 1/11* | (2006.01) |
| *H05K 1/09* | (2006.01) |
| *H05K 1/03* | (2006.01) |
| *H05K 13/00* | (2006.01) |

(52) U.S. Cl.
USPC ........... 174/262; 174/251; 174/255; 174/261; 174/268; 29/855

(58) Field of Classification Search
USPC ............. 174/251, 255, 261, 262, 268, 72 TR, 174/50.5, 71 R, 72 C, 72 R, 107, 110 R, 174/117 R, 113 R, 117 F, 117 FF, 151; 156/60; 361/749; 29/855
See application file for complete search history.

(56) References Cited

U.S. PATENT DOCUMENTS

| | | |
|---|---|---|
| 3,271,625 A | 9/1966 | Caracciolo |
| 3,922,777 A | 12/1975 | Weitze et al. |

(Continued)

FOREIGN PATENT DOCUMENTS

| | | |
|---|---|---|
| EP | 0660449 | 6/1995 |
| GB | 674484 | 6/1952 |
| WO | WO0067918 | 11/2000 |

OTHER PUBLICATIONS

Suaning, et al., Microelectronic Retinal Prothesis: III. A New Method for Fabrication of High-Density Hermetic Feedthroughs, *Proceedings of the 28th IEEE EMBS Annual International Conference*, New York, USA (2006), 4 pages.

(Continued)

*Primary Examiner* — Timothy Thompson
*Assistant Examiner* — Sherman Ng
(74) *Attorney, Agent, or Firm* — Clock Tower Law Group; Erik J Heels; Michael A Bartley

(57) ABSTRACT

A hermetic interconnect for medical devices is disclosed. In one embodiment, the interconnect includes platinum leads co-fired between alumina substrates to form a monolithic composite that is subsequently bonded into a titanium alloy flange. Both methodology for forming these interconnects as well as specific geometries and compositions are disclosed. Interconnects formed in this fashion enable significant reductions in overall size of the interconnect relative to the number of feedthrough leads as well as substantial improvements in robustness versus currently available technology.

29 Claims, 16 Drawing Sheets

(56) References Cited

U.S. PATENT DOCUMENTS

| | | | |
|---|---|---|---|
| 4,050,956 A | | 9/1977 | deBruin et al. |
| 4,375,379 A | * | 3/1983 | Luetzow .................. 156/52 |
| 4,501,929 A | * | 2/1985 | Escallier et al. .......... 174/117 F |
| 4,616,717 A | * | 10/1986 | Luetzow ................ 174/117 F |
| 4,991,582 A | | 2/1991 | Byers et al. |
| 5,059,558 A | * | 10/1991 | Tatsanakit et al. ............ 438/125 |
| 5,434,358 A | * | 7/1995 | Glahn et al. ................. 174/551 |
| 5,496,619 A | | 3/1996 | Itagaki et al. |
| 5,558,717 A | | 9/1996 | Zhao et al. |
| 5,643,835 A | * | 7/1997 | Chia et al. ....................... 29/827 |
| 5,782,891 A | | 7/1998 | Hassler et al. |
| 5,808,530 A | * | 9/1998 | Kalonji et al. ................ 333/260 |
| 5,869,784 A | * | 2/1999 | Shinchi ........................ 174/84 R |
| 6,041,496 A | * | 3/2000 | Haq et al. ......................... 29/852 |
| 6,146,743 A | * | 11/2000 | Haq et al. ....................... 428/210 |
| 6,414,835 B1 | | 7/2002 | Wolf et al. |
| 6,586,675 B1 | * | 7/2003 | Bealka et al. ............. 174/50.56 |
| 6,660,116 B2 | | 12/2003 | Wolf et al. |
| 6,662,035 B2 | * | 12/2003 | Sochor ......................... 600/378 |
| 6,666,821 B2 | | 12/2003 | Keimel |
| 6,985,347 B2 | | 1/2006 | Stevenson et al. |
| 7,174,223 B2 | | 2/2007 | Dalton et al. |
| 7,194,309 B2 | | 3/2007 | Ostroff et al. |
| 7,210,966 B2 | | 5/2007 | Taylor et |
| 7,211,103 B2 | | 5/2007 | Greenberg |
| 7,340,305 B2 | * | 3/2008 | Fischbach et al. .............. 607/36 |
| 7,464,717 B2 | | 12/2008 | Zhao et al. |
| 7,498,516 B1 | | 3/2009 | He |
| 7,535,693 B2 | | 5/2009 | Stevenson et al. |
| 2004/0149386 A1 | | 8/2004 | Numasawa et al. |
| 2006/0213955 A1 | * | 9/2006 | Watanabe ..................... 228/174 |
| 2006/0236533 A1 | | 10/2006 | Berry et al. |
| 2006/0283624 A1 | * | 12/2006 | Ok et al. ........................ 174/151 |
| 2007/0060969 A1 | | 3/2007 | Burdon et al. |
| 2007/0060970 A1 | | 3/2007 | Burdon et al. |
| 2007/0179553 A1 | * | 8/2007 | Iyer et al. ......................... 607/37 |
| 2007/0217121 A1 | | 9/2007 | Fu et al. |
| 2007/0236861 A1 | | 10/2007 | Burdon et al. |
| 2007/0239223 A1 | | 10/2007 | Engmark et al. |
| 2008/0049376 A1 | | 2/2008 | Stevenson et al. |
| 2008/0314502 A1 | | 12/2008 | Ok et al. |
| 2009/0159309 A1 | * | 6/2009 | Kanada et al. ............. 174/117 F |

OTHER PUBLICATIONS

International Search Report and Written Opinion dated Oct. 2, 2010 in related Application No. PCT/US2010/001635.

* cited by examiner

CO-FIRED METAL AND CERAMIC COMPOSITE FEEDTHROUGH ASSEMBLIES FOR USE AT LEAST IN IMPLANTABLE MEDICAL DEVICES AND METHODS FOR MAKING THE SAME

REFERENCE TO PROVISIONAL APPLICATION

This application is based on, claims priority to, and hereby refers to U.S. Provisional Patent Application Ser. No. 61/184,076, filed Jun. 4, 2009, the entire contents of which are incorporated herein by this reference.

FIELD OF INVENTION

The invention is a feedthrough for use principally (but not necessarily exclusively) in implantable devices, including implantable cardiac rhythm management (CRM) devices, neuro-stimulation devices, drug delivery devices or other implantable systems requiring an electrical feedthrough that also acts as a hermetic barrier between body fluids and electronics. Inventive feedthroughs can also be incorporated with batteries and electrolytic capacitors for implantable devices. The concept of attaching capacitors for EMI (electro-magnetic interference) filtering to these feedthroughs for the same applications is also part of the invention.

BACKGROUND OF THE INVENTION (1) U.S. Pat. No. 7,174,223 B2, Dalton et al. (Cochlear) describes direct bonded wire feedthrough leads for cochlear implants including the bonding of Pt leads into alumina ceramics and co-firing. Column 1 in the Background describes inserting pins into a green ceramic plate and sintering. The method described is one where pins are inserted into holes in the ceramic. Holes can be drilled, punched, pressed, etc. The process is labor intensive, has low manufacturing yields and cannot achieve the close lead-to-lead spacing that is available with the present invention.

(2) U.S. Pat. No. 5,434,358, Glahn and Montesano describes examples of high Temperature Co-fired Ceramic (HTCC) processing, which are typically utilized in applications other than biomedical implants, and do not typically use materials that are considered to be biocompatible. Traditional HTCC processing typically involves screen printing of inks onto ceramic tape but would not include co-firing of wires or metallic forms and would not be used as an interface between electronics and human body fluids (or in batteries or capacitors) in an implantable device. HTCC uses molybdenum or tungsten (and potentially their alloys) as leads—these are not appropriate for implantable systems due to concerns about corrosion in body fluids. HTCC technology further relies on vias, which for the purpose of this document may be defined as leads that are perpendicular to the plane of the substrates which make up a feedthrough. Vias have limitations with regard to lead-to-lead spacing, and suffer from diminished integrity of the ceramic substrates resulting from holes being pierced in them to form vias.

(3) U.S. Pat. No. 6,586,675 B1, Bealka and Decosta ("the '675 patent") describes brazed feedthroughs in which wire leads are brazed into metallized through holes using precious metal braze. These types of feedthroughs are appropriate where used, however issues of yield loss are associated with metallization and brazing of the lead seals. Metallization for the lead seals must extend beyond the lead, thereby increasing the size of the feedthrough and device.

(4) US patent application 2007/0217121 A1, Frysz et al. describes "integrated filter feedthrough assemblies made from low temperature co-fired (LTCC) tape" and relates to EMI filtering feedthroughs, and in general to construction of the capacitor itself.

(5) US patent application 2007/0060969 A1, Burdon et al. describes multilayer constructions with vias being "implantable co-fired electrical feedthroughs." Burdon et al. describes feedthrough lead connections ("vias") that are perpendicular to the direction of the ceramic tape or insulator layer. This type of construction is limited because the process of piercing the substrates and subsequently filling the vias is not reliable for producing a robust construction. Because of difficulties in the process of filling the via holes, hole-to-hole spacing cannot be reduced to the distances achieved in our invention. Some of their constructions show leads going through the ceramic not in straight paths, which is done to minimize the tendency of via feedthroughs to be non-hermetic. This approach consumes critical space within the feedthrough and thus the device. US patent applications 2007/0236861 and 2007/0060970 by the same authors are similar, and suffer from the same limitations due to the incorporation of vias. Note that paragraph 24 of 2007/0236861 states that the vias may be staggered through the substrates to improve integrity of the feedthrough—which in a roundabout way says that vias are not robust enough for the application without using up valuable space to offset the vias in a particular lead.

(6) Construction of high density feedthroughs for retinal prostheses are discussed in "Microelectronic retinal prosthesis: III. A new method for fabrication of high-density hermetic feedthroughs" by Suaning, G. J., Lavoie, P., Armitage, T., Forrester, J., Lovell, N. H., (2006), Proceedings of the 28th IEEE EMBS Annual International Conference, 30 Aug.-3 Sep., 2006, New York, USA. This method uses pre-sintered alumina substrates bonded together with alumina slip, and platinum metal traces. Very limited feedthrough geometries are available because of the use of fired substrates prior to bonding them together with leads. Fired substrates warp when re-fired, creating difficulties in closely matching and bonding the outer diameter of the feedthrough to inner diameter of the flange and hence difficulty in obtaining a hermetically sealed feedthrough. Our invention allows machining of the ceramic in unfired state, while this disclosure utilizes fired ceramic which is harder and more difficult to machine. Bonding fired substrates with slip is not very reliable as the slip will be constrained against shrinking in the plane of the substrates. Suaning et al. does not describe ink or wire patterns for forming leads as our invention does.

(7) US patent application 2008/0314502, Ok et al. "Method for Providing Hermetic Electrical Feedthrough" and US patent application 2006/0283624, Ok et al. "Method and Apparatus for Providing Hermetic Electrical Feedthrough" describe using vias of either ink or wire as leads running perpendicular to the plane of the ceramic substrate. The construction is similar to the multilayer constructions previously described, with the same limitations regarding center-to-center lead spacing and robustness of manufacturing process. The 2006/0283624 patent application is not essentially different than Dalton et al above, and the 2008/0314502 application seems very similar (with similar limitations) to the Burdon patents cited above in (5).

(8) U.S. Pat. No. 7,211,103 B2, Greenberg et al. describes a device that utilizes the feedthroughs from patents in (7) above, and suffer from the same limitations.

The entire contents of the documents identified in sections (1)-(8) above are incorporated herein by this reference.

SUMMARY OF THE INVENTION

The implantable device industry requires robust, small, biocompatible, inexpensive feedthroughs for cardiac rhythm management, neuro-stimulation and drug delivery devices. Current technology of brazed feedthroughs does not allow the very close lead-to-lead spacing or robustness desired because metalized space for bonding leads beyond the diameter of the lead is required. Typical pin brazing as described in the '675 patent, particularly for multi-pin feedthroughs, involves more complexity and risk of manufacturing yield loss. Co-fired technology as described in U.S. Pat. No. 7,174,223 B2 requires exacting tolerances between the through holes in green ceramic layers and leads and, as described in that patent, is labor intensive and lead center-to-center spacing is constrained by ability of the ceramic to maintain integrity through processing including punching of holes for leads. Via technology has the same spacing constraints and in addition to those, it is required to hermetically fill holes in green layers that have high length to diameter aspect ratios. Metallized ceramics with brazed in pins have potential failure mechanisms involved with braze flow and the metallization. Production of feedthrough ceramics by the disclosed methods will be less expensive and be more robust delivering lower cost and risk to the device market. Elimination of braze and metallization for typical pin seals makes the feedthrough much more resistant to corrosion which can cause hermeticity or electrical failure in the case of braze migration under applied voltage in a liquid environment.

There are applications where a high density pattern of leads is required, and for the implantable market, there is in general a trend toward smaller devices and smaller electrical feedthroughs. Current typical braze technology as shown in the '675 patent requires a metallization pattern that limits the proximity of the leads and via technology requires hole punching and subsequent filling that limits the number of leads and their reliability—while the aspect ratio of via diameter to length is critical. Spacing between leads is limited by the definition of the process for printing or placing them, so that lead to lead spacing as low as 0.0005" is possible in a particular plane (along the face of a substrate) utilizing the current invention. Spacing between layers of leads is limited by the ability to produce thin substrates with electrical integrity, which again for the sake of this invention we can put as low as 0.0005", for example. As typical braze feedthrough lead spacing with effort can get 0.035" because of required metallization braze and clearances between the lead and ceramic, this is a large reduction in size, which for the targeted applications is a huge advantage. Because of the potential high density of leads, applications for neuro stimulation where potentially hundreds or thousands of reliable feedthroughs are needed in a small area are possible. Low voltage feedthroughs can have very close lead spacings; a similar size reduction advantage is obtained for higher voltage feedthroughs because of the elimination of the metallization and braze. An inline pacemaker feedthrough ceramic as described in the '675 patent would have a width of approximately 0.080", whereas to achieve the same voltage standoff a feedthrough by this new methodology could be made with a 0.050" width assuming the design to remain essentially the same. The reduction in spacing advantage is increased when multiple layers of leads are employed. Utilizing a design shown in FIG. 1, it is envisioned feedthroughs as thin as 0.015" could be obtained, and utilizing a design similar to that shown in element 51, a feedthrough with a 0.010" diameter could be made. Limitations on thickness and diameter would fall to material handling requirements, rather than intrinsic limitations associated with prior art.

A purpose of the co-fired monolithic ceramic-to-metal composite is to form a feedthrough for implantable electronic connections either to protect electronics from exterior body fluids or to protect electronics from fluids inside an electrolytic capacitor or battery. Feedthroughs of the present invention allow for extremely close spacing between the electrical leads, resulting in a density of electrical connections previously not achieved by any conventional techniques. Typical applications will utilize the composite feedthrough structure of the present invention brazed or bonded into a flange which will subsequently be bonded to an electronics housing or directly into a housing for electronics or a battery or an electrolytic capacitor.

Implantable device voltages range from less than 1 volt to greater than 3 kV. Preferred embodiments of the invention would vary depending on the device requirement for voltage standoff, and connection(s) into and out of the medical device. Alumina has a voltage rating with safety factor better than 50V per 0.001" and so the materials themselves are not limiting for this invention. While the materials themselves in a theoretical environment for a 2.5 volt feedthrough would produce a lead to lead spacing of 2.5 microns, because of realities of producing the leads, insulating layers and subsequent connections to the implantable device, our invention is envisioned (conservatively) to be capable of producing lead-to-lead spacing of 0.0005" or greater. Decreased spacing may occur in some configurations.

These feedthroughs would be useful for both filtered (with an emi filtering capacitor) and non-filtered applications. This invention would be able to replace typical brazed feedthroughs in all of their usage in implantable devices. Connection to these feedthroughs where there is no lead extension might require metallization of the co-fired invention by typical thin film sputtering or thick film ink processing. Lead material could be brazed to the invention or connectors could directly contact the through traces. Connection to the leads to further electronics could take place by soldering, wire bonding, intimate contact through pressure, diffusion bonding or conductive epoxies. These are non-limiting examples of technology to connect to these leads. Because the leads in many forms of the invention are small in cross sectional area and do not extend beyond the surface of the ceramic, it is expected that device manufacturers would (or could) have connections that are different than what they are currently using.

Because of the very close lead to lead spacing capable of being produced, it is envisioned that metallization or connections applied to these feedthroughs could connect to one or more leads, and indeed a feedthrough with a repeatable matrix of electrically isolated leads spaced 0.0005" center to center (for example) would be capable of being connected to by larger connections with the requirement of precisely locating the individual feedthrough traces. 0.008" diameter (for example) connections placed randomly directly opposite each other would contact multiple leads forming electrical contact between those contacts and they would be electrically isolated from another similar pathway spaced (for example) 0.012" away center to center. Contacting more than one lead in the ceramic allows greater current carrying capability than contacting a single lead, and also imparts a safety factor as to connecting to a single lead.

Braze material could be sintered or melted onto traces of the invention to ease connection. Because the trace materials are refractory and the oxide ceramic matrix is capable of withstanding high temperatures, it may be possible to dip feedthroughs from the invention into molten gold or other suitable lead material. Any typical lead material with a melting point lower than the trace material could be brazed or sintered in place. In the case of the wire form of this invention it may be possible to directly wire bond or weld to the leads. The precious metals required or preferred as the basis of this invention have high conductivity per cross sectional area and are typically chosen for other implantable feedthrough applications because they are easy to solder and weld. It is not the purpose of this disclosure to limit connection methodology and connection technology available, however.

The invention could be used to make feedthroughs for batteries or capacitors for implantable devices. Because batteries and capacitors in these applications have the same general conditions as the feedthrough, that is a corrosive environment that needs separation from electronics, and the same advantages of this invention apply. As in the devices themselves, their batteries and capacitors need reliable feedthroughs and minimizing the cross sectional area through the various aspects of this invention would be advantageous in reducing the overall size and thickness of said batteries and capacitors.

Co-Firing of Pt or Pt alloy leads with the direction of the leads in the plane of multiple layers of green ceramic to simultaneously form a hermetically-sealed and electrically isolated implantable feedthrough. Platinum (or platinum alloy) "leads" are co-fired into ceramic. One feature of the present invention is that either fully dense platinum or Pt-containing ink is deposited onto layers of green (unfired) ceramic, followed by a subsequent layer of ceramic—with the possibility and intention of multiple layers of leads sandwiched between layers of ceramic. The green stack of ceramic with leads sandwiched inside is then compressed and fired to densify the ceramic, and simultaneously form hermetic seals between the ceramic and the Pt or Pt alloy lead material. (In at least some contexts of the invention, "hermetic" may generally mean that a feedthrough is capable of isolating an environment on the outside of a device from the inside of the same device.)

Forming of the ceramic composite feedthrough body. While it is not required that the green ceramic starting layer be "tape" as typically used in HTCC or LTCC processing, typical tape processing can be used for this invention. Thin layers of ceramic may also be pressed to low pressure, followed by repressing at higher pressures prior to firing (sintering). Similarly, layers of ceramic can be laid down in a slurry form (and dried) alternated by layers of leads, which can be laid down in slurry form (e.g. by full-area or partial area screen printing), vapor deposited, or in solid or dense form. Utilizing ceramic tape common to HTCC processing, very thin layers of ceramic can be used, allowing very tightly spaced lead configurations. Layers of ceramic can be vapor deposited and layers of metallization can also be vapor deposited, allowing for extremely tight spacing of leads. It is not required that "tape" be used. Shaped layers can be utilized allowing features for alignment of the leads or features that are beneficial to brazed feedthrough configuration, or that aid in alignment for typical ceramic machining to get a feedthrough suitable for subsequent brazing; this might include forming depressions in the unfired ceramic substrate which would aid in placement of the feedthrough leads. Note that the cross sectional area of the "lead" can be modified depending on required voltage, attachment methodology or safety factor. Leads can be a series of wires or could be formed from a patterned sheet of platinum which would define lead center-to-center spacing. The ceramic layer could be flat or have grooves in which the wires are placed prior to compaction into a stack to facilitate alignment and bonding. In any of the constructions discussed, a grounding pattern can be incorporated where one or multiple leads make contact with the outer diameter of the monolithic ceramic metal composite feedthrough.

Machining of the unfired or fired composite feedthrough. Once the multilayer stack of ceramic/leads/tape is formed, conventional machining techniques can be used to form the multilayer stack so that it will have appropriate thickness and outer diameter for sealing into a flange or into a housing for an implantable device. It is a benefit of the invention in some embodiments that multiple composite feedthroughs can be made from the same blank of material.

Multiple ceramic feedthroughs could be made from the same tape stack by slicing "wafers" from a longer stack before or after firing. The stacks may be further formed before or after firing (see FIGS. 2 and 6) to get desired feedthrough thickness and ceramic shapes (see FIG. 4).

Varying feedthrough constructions and forms. A very simple thin feedthrough can be made with 2 or 3 layers of ceramic. By patterning pads on the outside of the ceramic that are either connected over the ends of the interior/exterior faces of the ceramic or connected through the ceramic through vias, surfaces are presented that can be connected to by standard electrical connectors, wire bonding, soldering or brazing. While the drawing in FIG. 1 shows a co-fired metallization making the connection to the traces between the sheets, a post co-fire metallization can just as easily be applied to accomplish the same goal.

Various leads using patterned and co-fired platinum ink could be used, as well as platinum wire or patterned sheet, as illustrated in FIGS. 1, 2, 3, 4 and 6. There are a multitude of variations in feedthroughs available by combining different forms of the invention as described and as shown in the various figures. A need for an interposer such as those shown in FIG. 7 could be satisfied by using the foil forms shown in FIG. 6 and then extending the leads as shown in FIG. 3. One could combine foil, wire, and metal ink leads and still be within the scope of the invention. While it is not illustrated, a further form of the invention could use hollow wires rather than solid ones.

Embodiments of the present invention can incorporate leads that extend beyond the surface of the ceramic depending on the proposed mechanism of connection to the feedthrough. A simple feedthrough would include 2 layers of ceramic sandwiching a pattern of wires, allowing for a very thin feedthrough, with the possibility of tight lead center-to-center spacing. The concept can be extended to one or multiple layers of leads. For leads that extend, an advantage would be gained by using Pt alloys rather than pure Pt that anneals and gets very soft when exposed to the temperature needed to fire the green ceramic.

A grounded trace such as that shown in prior art FIG. 8 can be incorporated into the brazed feedthrough either by using the invention as described by Bealka et al, or by including a lead in the composite feedthrough that contacts the brazed flange.

An alternate form of invention is illustrated in FIG. 5. A different way of making the feedthrough ceramic would be to alternately screen coatings of ceramic oxide and metal leads, then co-fire to build a composite stack containing multiple layers without using preformed insulator layers and subsequent pressure to make a monolithic ceramic compact. This method provides the advantage of potentially achieving an outer diameter that is rounded or closer to final size, compared to the tape method which would likely require machining after its initial compaction and firing. Given a biocompatible material or alternating layers of materials of dielectric it would be a way of making a biocompatible capacitor that doubles as a feedthrough. This product configuration could be composed of zirconia, alumina, or titania ceramic layers (or combinations thereof). Powder suspensions are applied layer-by-layer and an outer diameter metallization could be incorporated into the co-fired composite. A grounded lead or grounded leads could be attached to the outer diameter of the ceramic by a connecting trace as are typically used in multilayer capacitors. Emi filtration can be built into the composite feedthrough by grading insulator layers such that a body facing insulator material would be more conducive to contact with human tissue (for example) like alumina, and internal layers would have dielectric properties conducive to emi filtration (for example) like titanates.

This construction is different from other embodiments of the invention because the feedthrough leads are not desirably formed parallel to the plane of the ceramic substrate. By silk screening down thin layers or patterns of ceramic and alternating these patterns with metallic patterns that fill in holes in the ceramic pattern, leads can be built in patterns that are perpendicular (or otherwise angled) to the plane of the screened ceramic "substrate" without the requirement to form vias.

Sealing the composite feedthrough body to a flange. Once the multilayer stack of tape/leads/tape is fired, conventional sealing techniques can be used to bond the multilayer stack into a flange, including subsequent metallization similar to that used in the '675 patent, bonding by active brazing alloys (e.g. Wesgo ABAs as non-limiting examples), glass or glass ceramic sealing, compression bonding or other sealing techniques. One or more of theses composite feedthroughs could be sealed into an individual flange or device.

An advantage of the present invention: very close lead-to-lead spacing. The invention allows very close lead-to-lead spacing in a reliable package for implantable applications. To take advantage of closest lead center-to-center spacing enabled by this invention, leads are essentially straight through from the electronics side of the device to the body side of the device. Typical brazed feedthrough wires require metallization that extends beyond the outer diameter of the lead wire onto the ceramic to facilitate the ceramic-to-metal bonding by gold or some other biocompatible braze alloy. The present invention is potentially much less expensive than current brazed ceramic-to-metal feedthrough technology and should produce more reliable feedthroughs by eliminating typical braze joints associated with leads. A significant part of the overall expense of conventional brazed feedthroughs is associated with yield loss throughout the manufacturing process. The process of the present invention is more robust by eliminating the need to braze ceramic-to-metal leads in difficult geometries that are encountered, especially with close lead spacings.

A thrust of this invention is to provide a co-fired composite that replaces conventional feedthroughs that utilize either ceramic, glass ceramic, or glass based insulators, in biocompatible applications including those where batteries and wet capacitors are used in association with a medical device. Further, the feedthrough provides a barrier between body fluids and the device components.

While FIG. 1 shows a geometry that is conducive to connection with a typical connector, or wire bonding or solder, etc., the geometries presented are intended to be non-limiting. It is expected that the co-fired composites would be further processed to include metallization patterns appropriate for subsequent brazing, soldering, wire bonding, or other method of obtaining intimate contact of wires or connections to electronics or electrical leads.

It is also envisioned that feedthroughs of the present invention will have capacitors for emi filtration attached to them in some devices.

Because of the close lead center-to-center spacing allowed with the technology, it is envisioned that feedthroughs such as shown in FIG. 4 element 46, and FIG. 5 element 56 could be used as a "standard" feedthrough. If a feedthrough with a matrix of leads is available in a very small size, then based on specific application requirements, a designer could choose the number of leads to connect, and by using multiple leads for the same connection, achieve a lower electrical resistance path. The width and thickness of the leads can vary dependant on required operating voltage. Leads continuous to the outer diameter of the composite feedthrough and are then connected to the braze joint into the metallic flange could be electrically grounded to the flange.

In addition to platinum, platinum family materials and platinum alloys as well as refractory metals such as Nb and Ta and their families could be used as well. Alloys of Mo, W, with biocompatible metals such as platinum or palladium could also be used for this invention. Alloys of precious metals with refractory metals would be desirable for wires as the strength of pure precious metals in annealed state is relatively low in comparison to pure platinum. Ceramics made of alumina and its alloys are the preferred embodiments of the invention, however zirconia, and titania and composite materials of alumina, titania and zirconia, as well as other materials, could also be used.

The invention is valuable at least because it provides a robust seal design compared to available technology, eliminating wire lead seal braze joints, wire lead seal glass or wire lead glass ceramic seals, or electrically conducting vias.

The invention also is valuable at least because it minimizes required space per required lead at a given voltage stand-off, allowing for higher quantity lead densities or overall smaller feedthroughs (or both).

For example, typical brazed feedthroughs described in the '675 patent require metallization and braze beyond the lead to make a good hermetic bond. The extent of this metallization dictates the minimum spacing between leads as well as the width of the feedthrough. The metallization can be a costly step and can be prone to hermetic failure. The invention removes space required from metallization and also removes the complexity and weakness potentially associated with metallization at the leads. The other teachings of the '675 patent are incorporated into this invention.

"Direct bonded" feedthroughs as described in U.S. Pat. No. 7,174,223 above require a high degree of manual labor as described in the referenced patent. The method of the current invention is more easily adapted to automation and requires less labor. Piercing the green ceramic layers can be labor intensive and because of the fragile nature of green ceramic, the through-hole spacing and hence spacing between electrical leads is much larger than what is possible with the current invention. Because the direct-bonding process relies on the ceramic shrinking onto the lead to form a hermetic bond the size and shape of the hole in the green ceramic as well as the diameter of the lead (the fit between the two) must be tightly controlled. The invention allows reforming of the ceramic after the leads are in place to ensure the ceramic is robust.

"Typical Multilayer" as described in US 2007/0060970 A1 provides for manufacture of feedthroughs in which the multilayer relationship is obtained by piercing the green ceramic layers, and is then subject to the same restrictions and problems as detailed in direct bonded method above. In addition to these limitations typical co-fire requires that metallization filled vias be, filled. This effectively limits the length of the feedthroughs due to difficulty completely filling small diameter relatively long holes with a dense metallization. With the invention, very small cross sectional area leads can be obtained in a robust manor.

The construction proposed by Suaning et al. is limited to bonding fired substrates together with slip. This method is not likely to provide a robust reproducible product, and does not allow for flexibility in design parameters, unlike the current invention. In Suaning et al., all machining would occur after firing of the ceramic, flatness problems would be encountered with fired substrates, and the method would not have the flexibility enjoyed by the ceramic tape process of the current invention. The bonding fit of Suang would contract in all directions when fired, and would be constrained by the fired substrates causing voiding and potential leak paths.

Consistent with Various of the Appended Claims, Versions of the Invention May be Described as:
A feedthrough comprising:
a. a first insulative component having at least one bonding surface;
b. a second insulative component bonded to the first insulative component at the bonding surface; and
c. a conductor disposed between the first and second insulative components along at least a portion of the bonding surface.

Likewise, versions of the invention may be described as:
A feedthrough comprising:
a. an insulative component; and
b. first and second conductors electrically isolated from each other by the insulative component and having center-to-center spacing of less than 0.018 inch.

Additionally, versions of the invention may be described as:
A method of forming a feedthrough comprising:
a. providing a first insulative component with at least one bonding surface;
b. providing a second insulative component;
c. disposing a conduct between the first and second insulative components and along at least a portion of the bonding surface;
d. bonding the first and second insulative components at the bonding surface;
e. exposing a portion of the conductor.

DETAILED DESCRIPTION OF THE DRAWINGS

Figure 8:
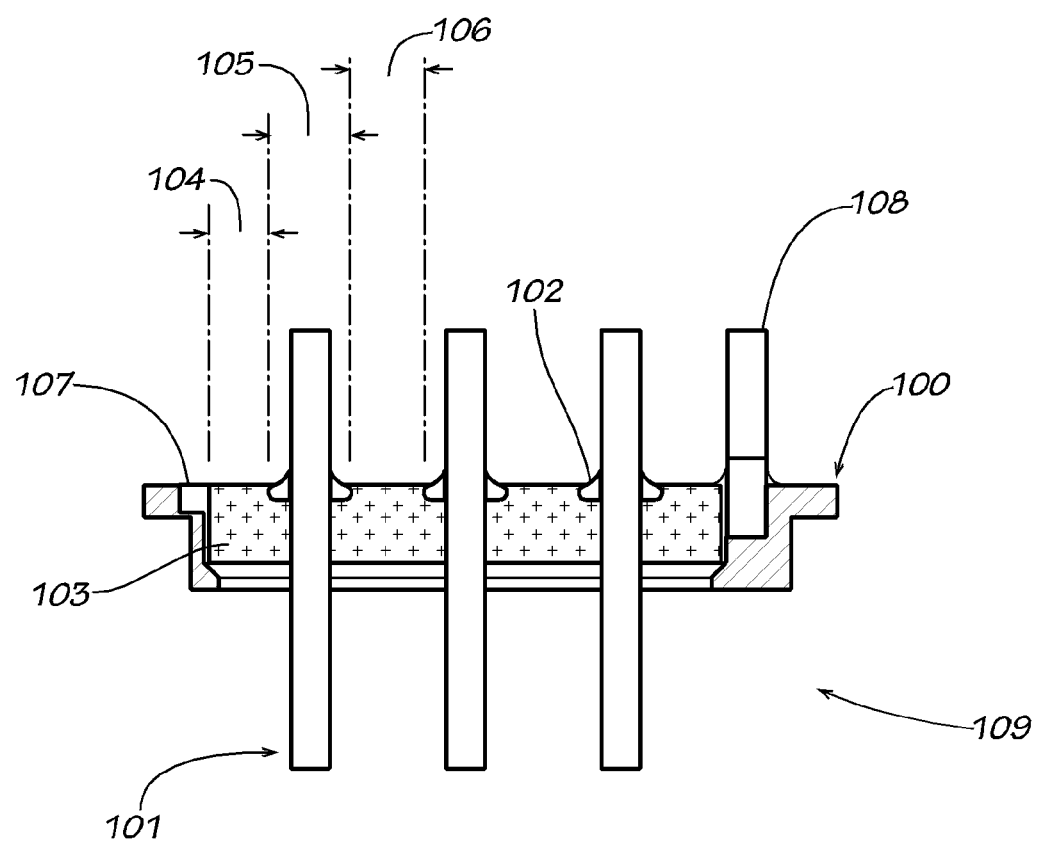
FIG. 8 is a cross-sectional view of an existing (prior art) feedthrough.
Figure 9:
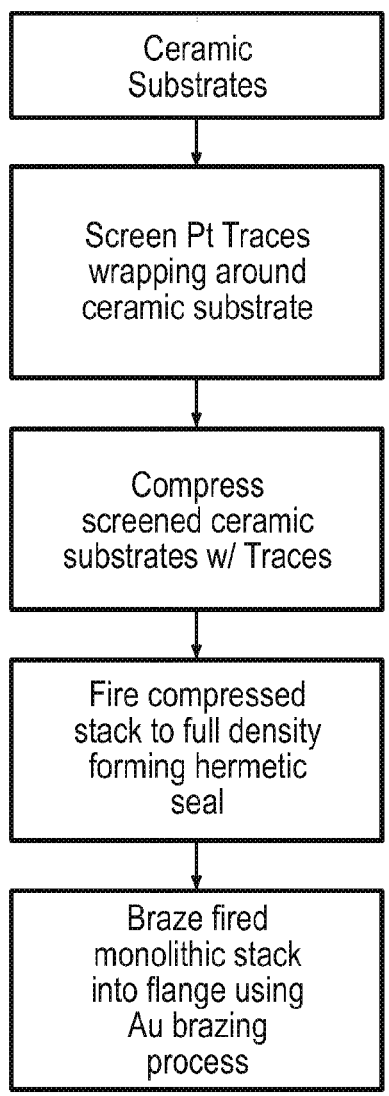
FIG. 9 is a flow chart identifying certain steps useful in connection with formation of the feedthrough of FIG. 1.
Figure 10:
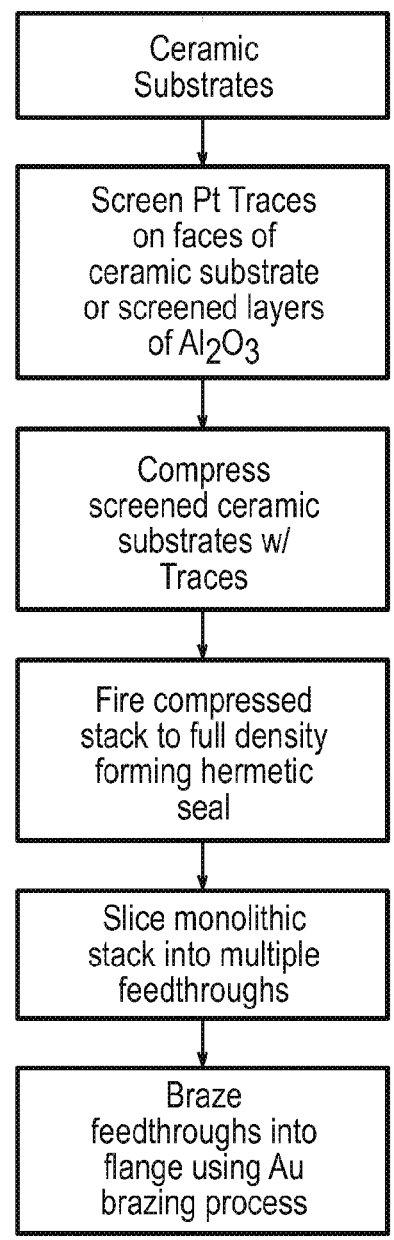
FIG. 10 is a flow chart identifying certain steps useful in connection with formation of the feedthrough of FIG. 2.
Figure 11:
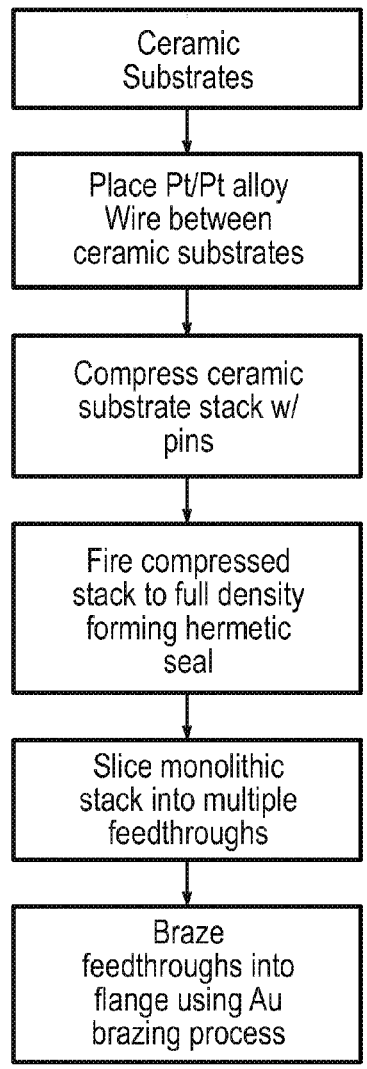
FIG. 11 is a flow chart identifying certain steps useful in connection with formation of the feedthrough of FIG. 3.
Figure 12:
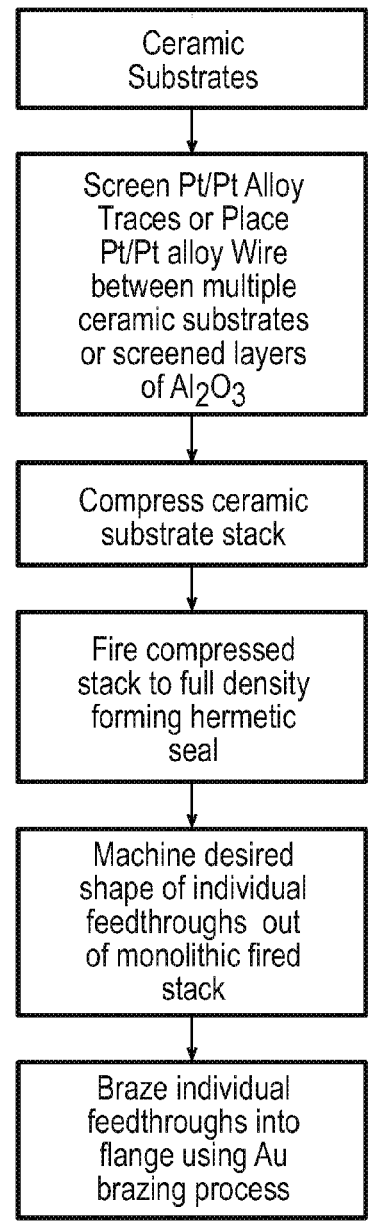
FIG. 12 is a flow chart identifying certain steps useful in connection with formation of the feedthrough of FIG. 4.
Figure 13:
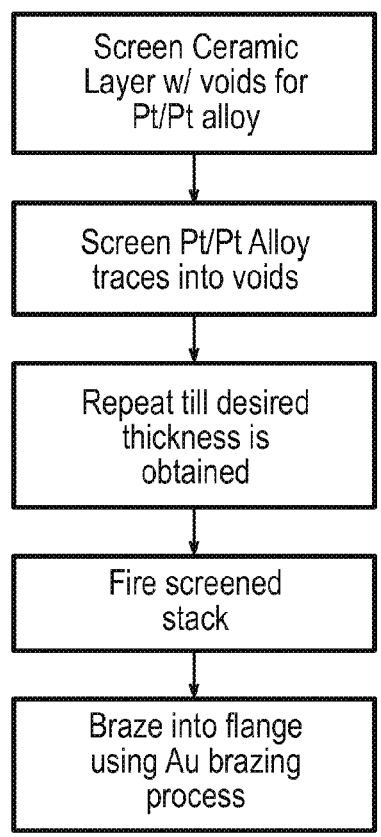
FIG. 13 is a flow chart identifying certain steps useful in connection with formation of the feedthrough of FIG. 5.
Figure 14:
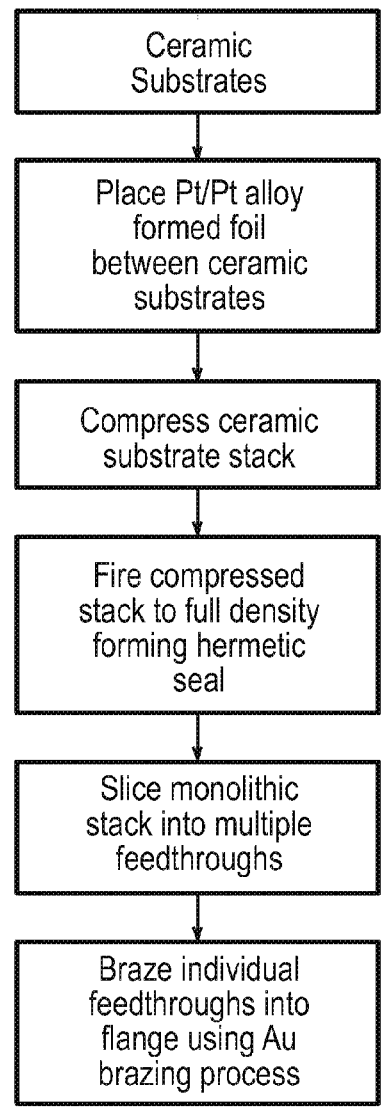
FIG. 14 is a flow chart identifying certain steps useful in connection with formation of the feedthrough of FIG. 6.
Figure 15:
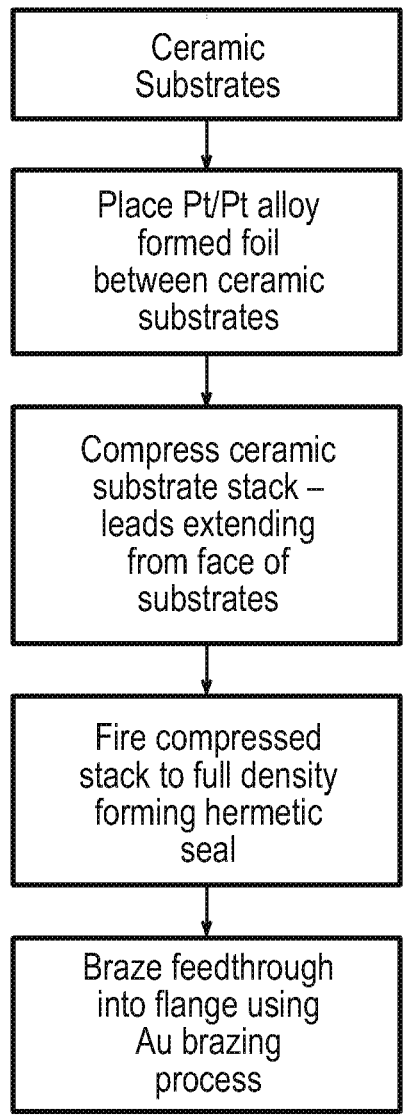
FIG. 15 is a flow chart identifying certain steps useful in connection with formation of the feedthrough of FIG. 7.
Figure 16:
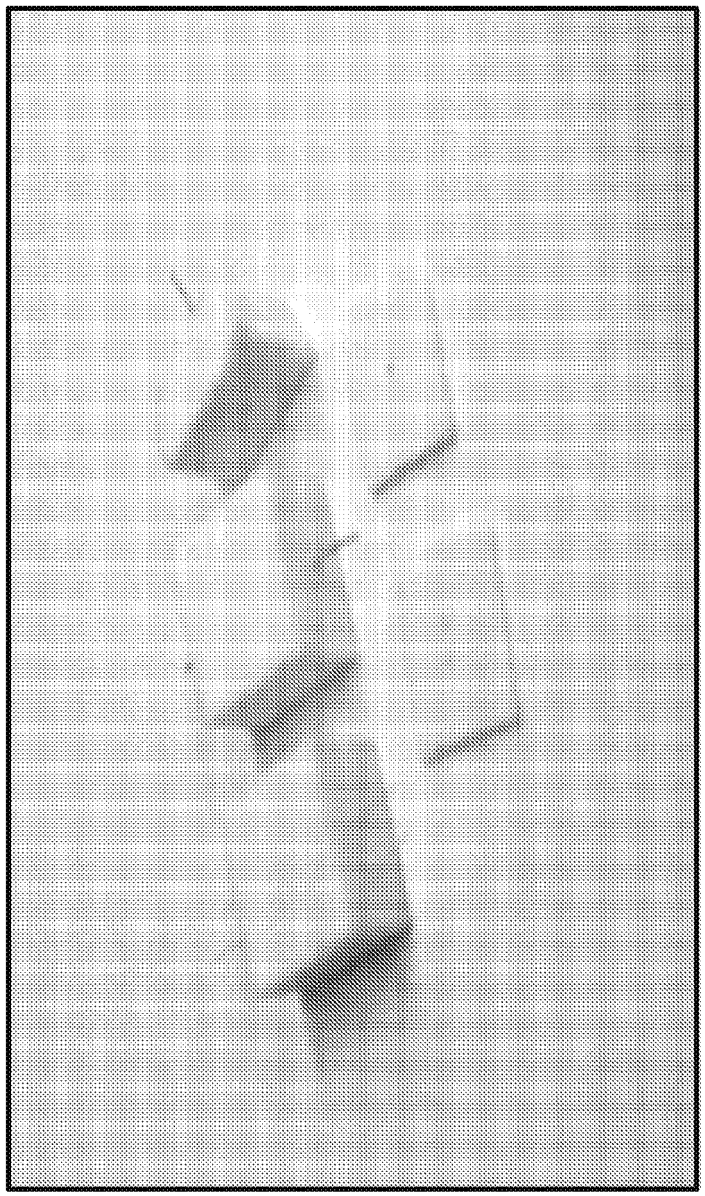
FIG. 16 is a photograph of a 0.004" diameter platinum bipolar feedthrough made in using the present invention.
Figure 17:
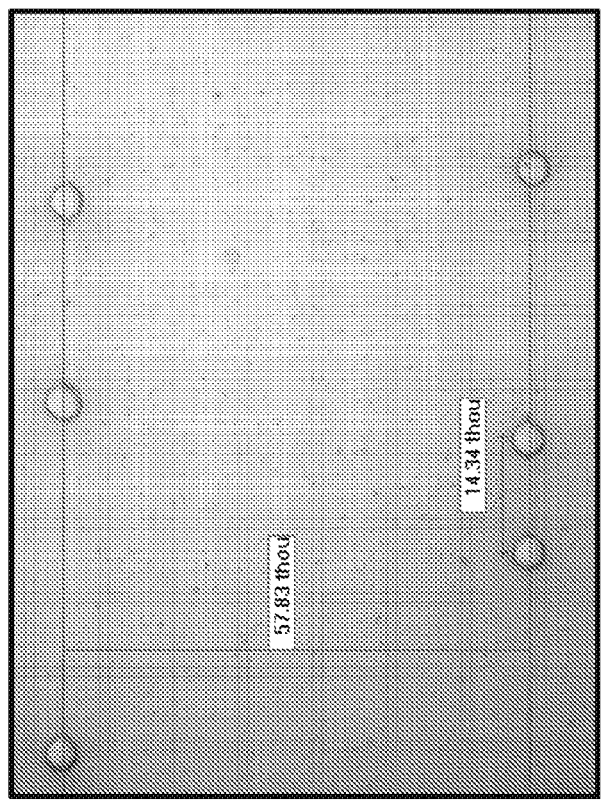
FIG. 17 is a photograph showing 0.004" diameter platinum leads sintered into alumina sectioned perpendicular to the axis of the leads. Minimum lead center to center spacing of approx 0.014" is illustrated.
Figure 18:
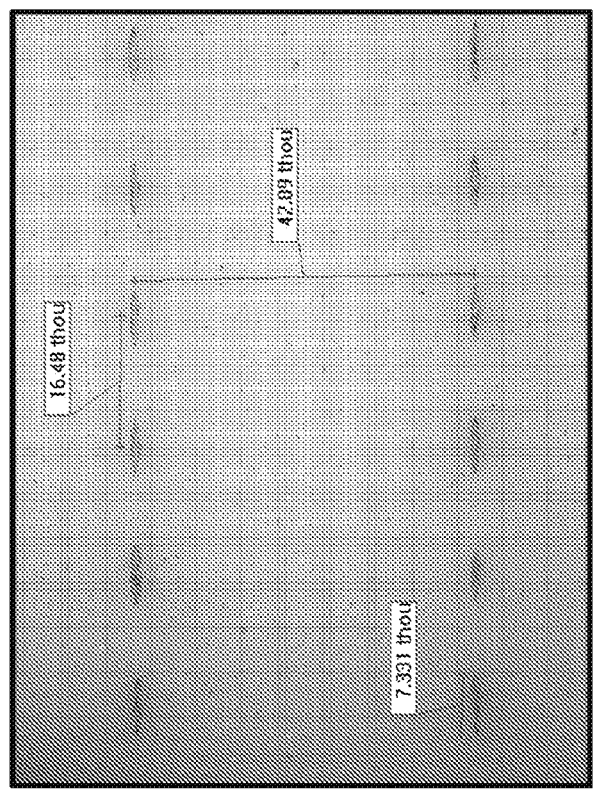
FIG. 18 is a photograph showing 0.007" wide sintered platinum ink leads sintered into alumina sectioned perpendicular to the axis of the leads. Minimum lead center to center spacing of approx 0.016" is illustrated.
Figure 19:
FIG. 19 is a photograph showing approx. 0.004" wide sintered metal ink leads sintered into titanate ceramic sectioned perpendicular to the axis of the leads. Leads are spaced approx 0.006" center to center within each layer and approx. 0.004 center to center between layers.
Figure 20:
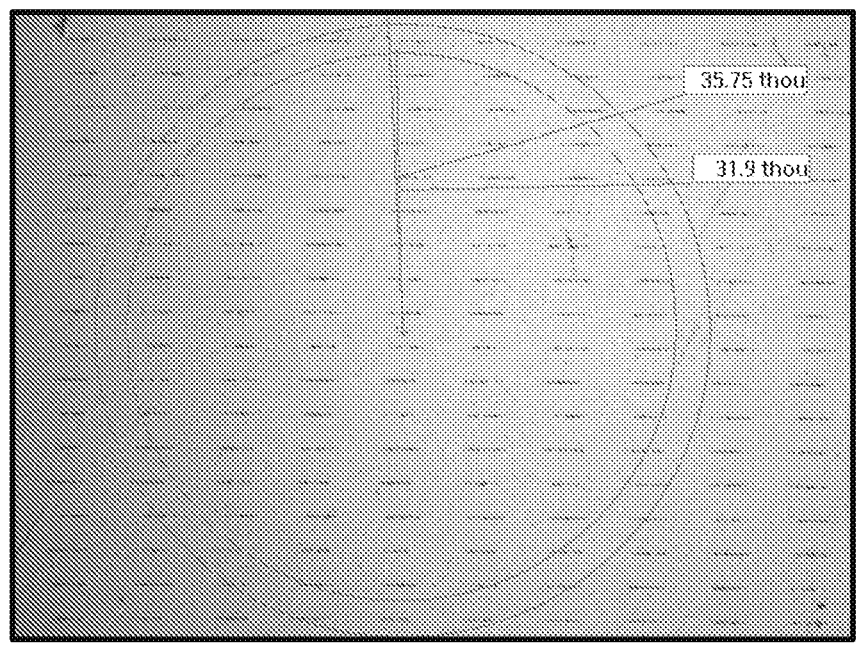
FIG. 20 is another photograph similarly to FIG. 19 illustrating clearly that a large quantity of leads can be obtained in a very small area.

Prior Art FIG. 8 shows brazed feedthrough 109 per Bealka and DaCosta '675 patent. Three feedthrough wires are brazed into a metallized ceramic with gold braze. The ceramic and another wire are brazed to a titanium outer flange with gold.
100—Titanium flange brazed to the outer diameter of ceramic 103, ground wire 108 with gold 107. In the areas where gold bonds to 103, a layer of metallization has been applied to 103 prior to braze.
101—Platinum feedthrough wire shown 3X brazed into ceramic 103 with gold 102.
102—Gold braze bonding feedthrough wire 101 to ceramic 103.
103—Insulator alumina ceramic.
104—Insulating distance between gold braze 102 used to bond feedthrough wire 101 into ceramic 103 and gold braze 107 bonding flange 100 to the outer diameter of ceramic 103.
105—Diameter of gold braze shown beyond feedthrough wire 101 required to form a seal.
106—Insulating distance between adjacent gold braze fillets at feedthrough wire(s) 101.
107—Gold brazed used to bond flange 100 to ground pin 108 and ceramic 103.
108—Ground pin brazed to flange 100 and ceramic 103.
109—Brazed feedthrough typical of prior art.

Note: This construction is typical of the majority of existing prior art. Feedthrough lead wires 101 are typically a minimum of 0.006" in diameter, both for ease of handling and because the gold braze used to bond the leads to the ceramic alloys with or dissolves the metal lead. The diameter of gold 105 surrounding the lead is typically 0.030" at minimum, and reducing this diameter results in increased yield losses and difficulties in getting the gold to wet to the metallized ceramic. Because there are tolerances in the ceramic manufacturing methods and application of metallization, the insulation distances 104 and 106 would typically be a minimum of 0.008". The lead density, which is controlled by lead-to-lead center-to-center spacing is then 0.008"+0.030", or 0.038", which is much larger than the potential minimum lead-to-lead spacing of 0.0005" enabled with the present invention.

Figure 1:
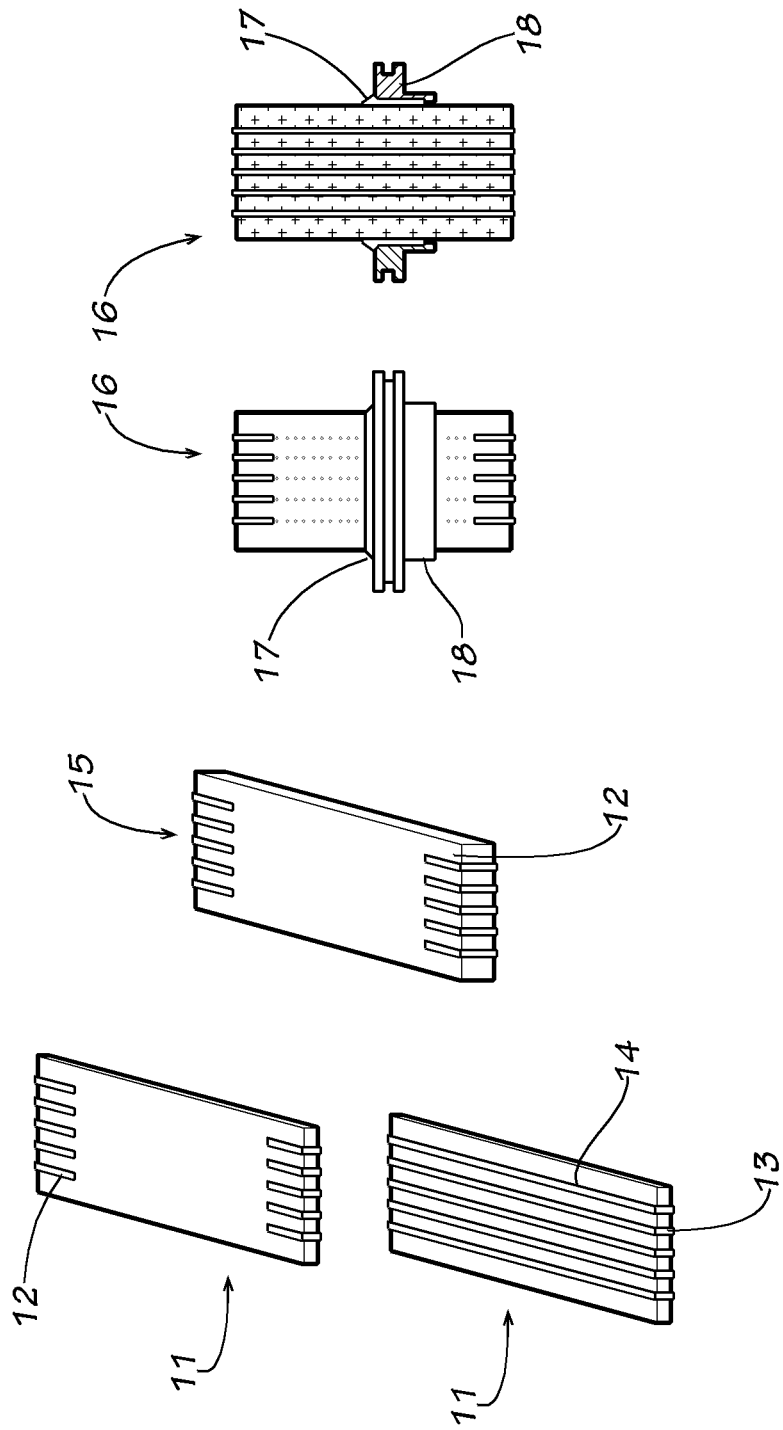
FIG. 1 is a set of views of an exemplary terminated-connector feedthrough.

Terminated Connector Feedthrough FIG. 1 shows a feedthrough constructed with two identical substrates that are patterned parallel to the axis with platinum ink. Metallization goes over the ends of the substrates onto the opposite faces to form an area that is easy to bond on the outer diameter of the feedthrough by solder, braze, wire bond, standard connector, etc. By inserting a blank substrate (31, FIG. 3) between elements 11, one could double the number of isolated leads. Similarly by substituting blank substrate 21 (FIG. 2) for one of the element 11 substrates, the feedthrough would only have connections on one outer diameter face.

11—Insulator substrate patterned with metal particulate—not sintered or fully densified.

12—Metallic pattern continuous with 13 or connected through via to 14.

13—Metallic pattern continuous with 12 and 14.

14—Metallic pattern continuous to both ends of substrate and 13

15—Sintered monolithic composite feedthrough made from (2) pieces of 11, with 5 through leads as shown

16—section and normal views of a brazed feedthrough made with 15, 17, 18.

17—Braze material joining flange 18 to feedthrough ceramic 15.

18—Metal flange brazed to feedthrough ceramic 15 using braze 17.

Note that drawings show a non limiting example. While this has only one layer of through traces, using a third unpatterned substrate between the layers of 11 would double the number of isolated leads. The number of traces could range from one to many. Using the foil concept shown in FIG. 6, the same feedthrough shown as element 15 could be produced, whereby the foil would be sandwiched between the substrates, folded over the ends, the individual pieces would be bonded by pressure followed by sintering. Terminations as shown for elements 12 and 13 could be applied prior to sintering of the feedthrough or afterwards, utilizing a typical metallization system.

Figure 2:
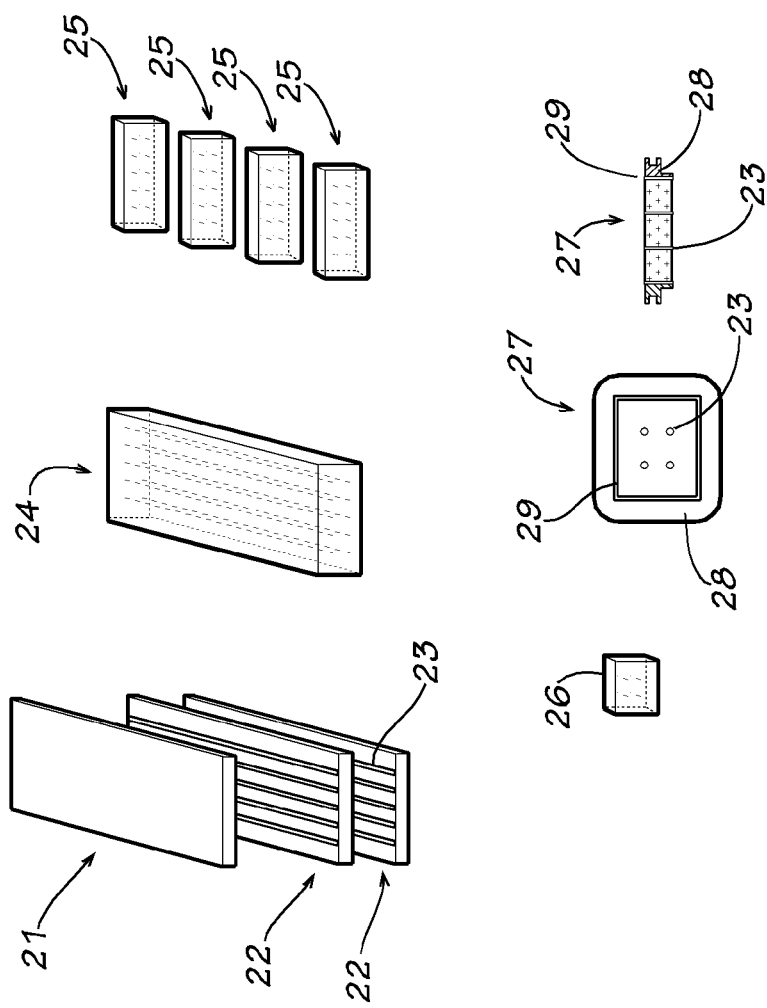
FIG. 2 is a set of views of an exemplary non-terminated connector feedthrough.

Non Terminated Feedthrough FIG. 2 shows a feedthrough similar to that of FIG. 1, except that there is no metallizing connection onto the outer diameter faces for connection. While this embodiment shows two layers of leads, the number of layers of leads could range from one to many. The finished shape of the feedthrough 25 is typically rectangular, but through fired or unfired machining could easily be any brazable shape. It is envisioned that very thin hermetic feedthroughs could be manufactured by machining feedthroughs shown in element 25 to thicknesses as thin as 0.008"—this is possible because of the monolithic nature of the fired substrates as opposed to prior art constructions.

21—Insulator substrate—not sintered or fully densified.

22—Insulator substrate patterned with metal particulate—not sintered or fully densified. Five separate metallic traces are shown going the length of the substrate.

23—Metallic traces on surface of 22

24—Sintered monolithic substrate made of 2 layers of 22 and a top layer of 21

25—Sections of 24—ceramic feedthroughs

26—A section of 25—ceramic feedthrough

27—Two views of a feedthrough made with ceramic feedthrough 26, metal flange 28 and braze 29.

28—Metal flange.

29—Braze material.

Note that drawings show non-limiting examples. While this has two layers of through traces, the construction could have been one layer of traces or many, and the traces per layer could range from one to many.

Figure 3:
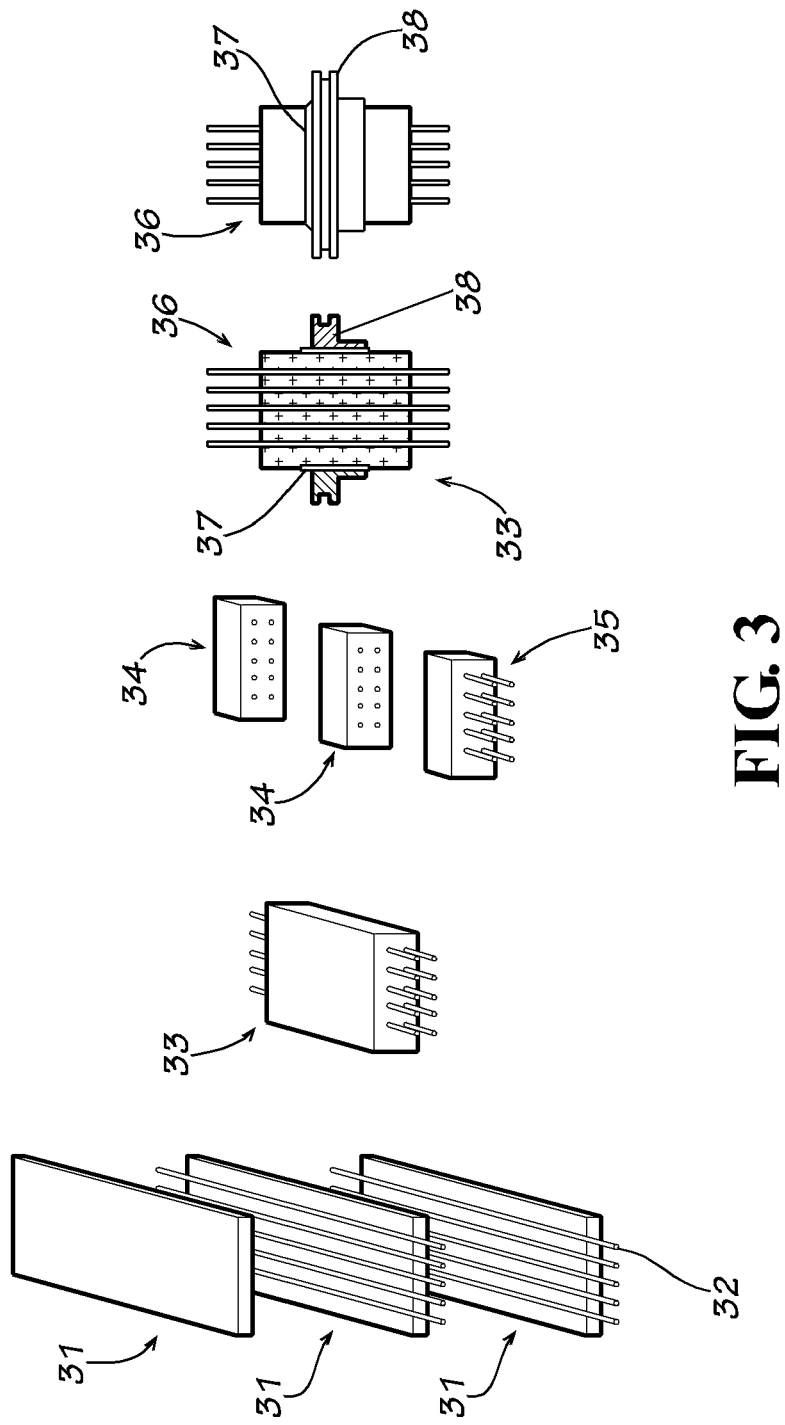
FIG. 3 is a set of views of an exemplary wire feedthrough.

Wire feedthrough FIG. 3 shows a feedthrough made with platinum or platinum alloy wires (preferred). While the feedthrough in 36 shows wires extending, it is envisioned feedthroughs such as those shown in elements 34 and 35 would be desirable in many cases depending on how subsequent electrical attachments are to be made. As with other embodiments, one layer of leads or many can be utilized and the number of leads per layer can range from one to many.

31—Insulator substrate—not sintered or fully densified.

32—Metal wire(s) placed onto 31.

33—Monolithic ceramic/wire composite made of 3 layers of 31 sandwiching two layers of (five each) 32—ceramic feedthrough.

34—Sections of 33 showing through wires flush with face of ceramic—ceramic feedthrough

35—Section of 33 showing wires extending on one face with wires flush on second face—ceramic feedthrough.

36—Two views of a brazed feedthrough made of 33, flange 38 and braze 37.

37—Braze material.

38—Metal flange.

Note that drawings show a non limiting example. While this has two layers of through traces, the construction could have been one layer of wires or many and the number of wires could range from one to many. Note that "wires" could be individual or connected flat ribbons.

Figure 4:
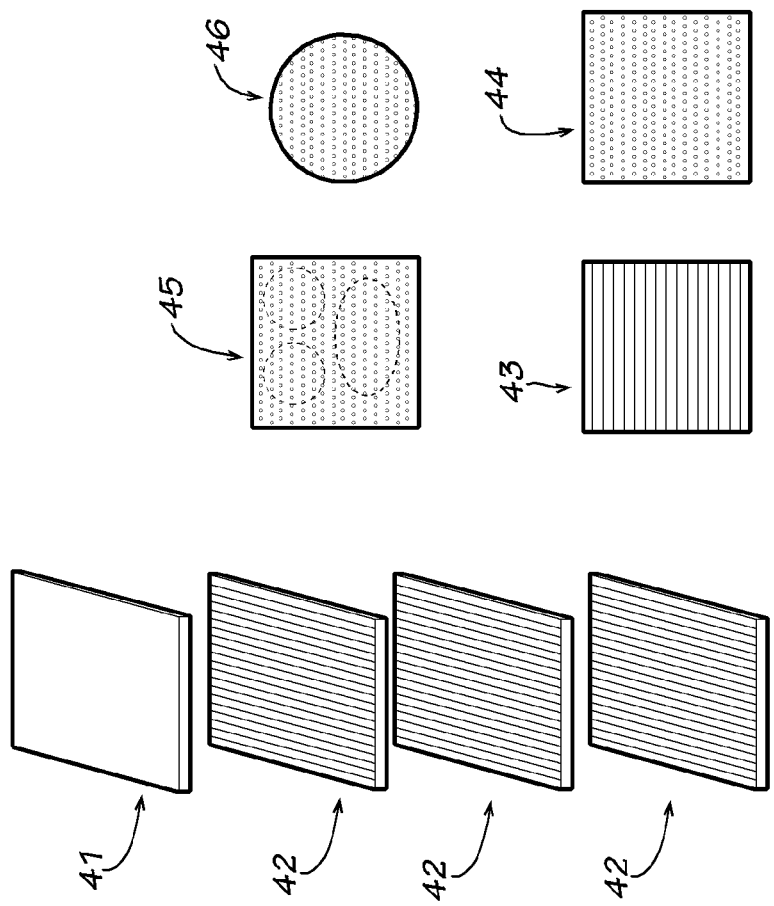
FIG. 4 is a set of views of an exemplary composite ceramic for a generic feedthrough.

Composite ceramic Construction Blank FIG. 4 shows construction of a composite ceramic for a generic feedthrough. The composite is built layer by layer, either with metallized substrates as described in FIG. 2, or with wires or foil as described in FIG. 3 or 6. The unfired substrates with metal patterning are pressed together as shown in element 43, becoming substantially monolithic in element 44. In element 45, it is shown that various shapes can be machined from this monolith either in the fired or unfired state. Element 46 shows an end view of a generic feedthrough. For example—if element 44 represents a 1"×1"×1" cubic monolith and element 46 represents a 0.9-inch diameter feedthrough that is 0.030" thick with leads that are spaced 0.006" center-to-center, it is easy to see that many leads will be available regardless of where the exact machining of the outer diameter is relative to the lead pattern. Multiple feedthrough monoliths will be able to be sliced/machined from each 0.9-inch diameter blank. Similarly, if multiple 1-inch diameter monoliths were machined from the cubic monolith it would provide multiple isolated leads.

41—Insulator substrate—not sintered or fully densified.

42—Insulator substrate patterned with metal particulate or wires or foil, and the substrate not sintered or fully densified. Multiple separate metallic traces shown going the length of the substrate.

43—Multiple layers of 42 covered with a layer of 41—frontal view only.

44—Sintered monolithic ceramic feedthrough comprised of 43—frontal view only.

45—44 showing examples of feedthrough shapes machined from 44 in either sintered or unsintered state—frontal view only.

46—Round composite feedthrough showing multiple conductive traces—frontal views only.

Note that drawings show non limiting examples. Number of conductive traces per finished shape could range from one to many, and shapes machined from monolithic structure 44 could range from one to many and their shapes could vary from those shown. Drawings of brazed feedthroughs not included, but same concept as in FIGS. 1, 2, 3, 5.

Figure 5:
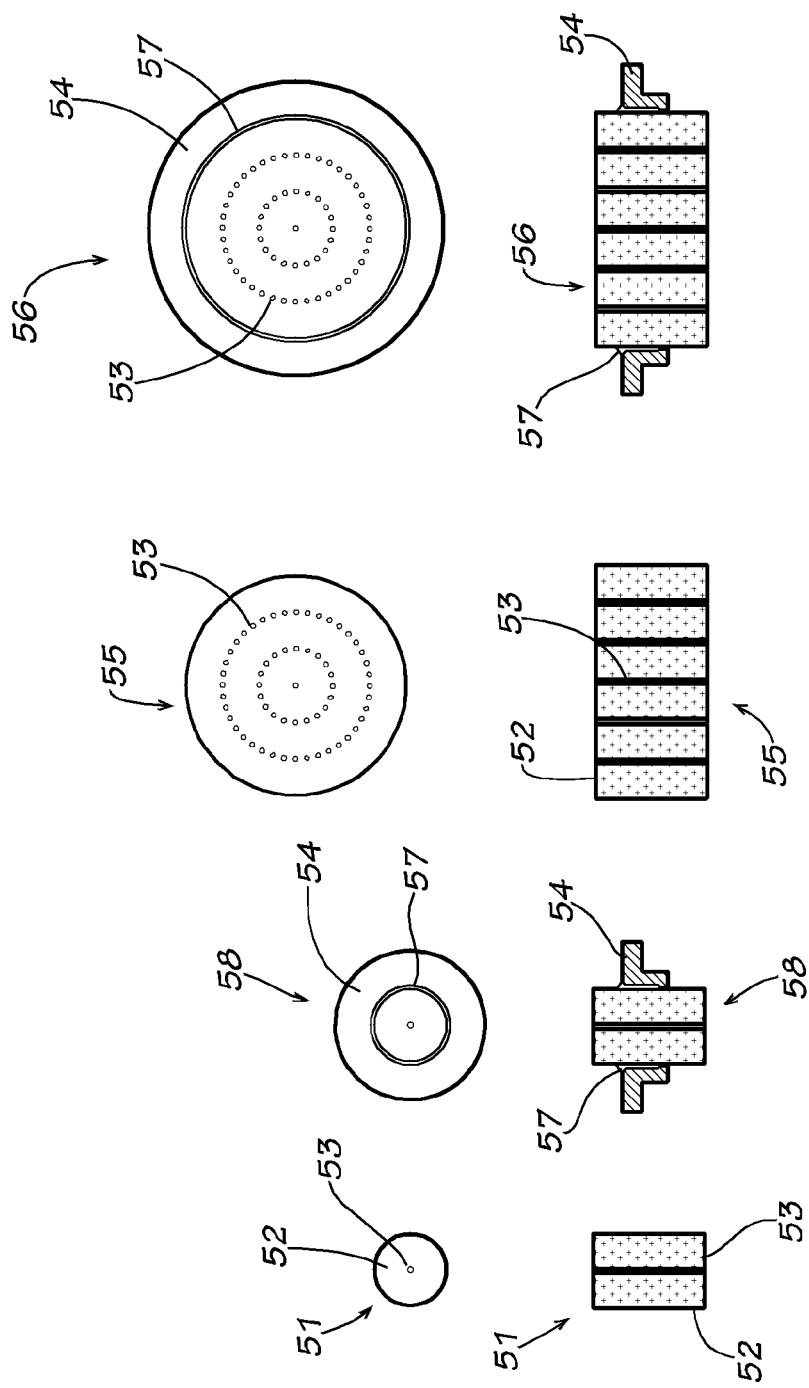
FIG. 5 is a set of views of an exemplary feedthrough formed by depositing layers of both conductive and insulative material.

Alternate Construction Feedthrough FIG. 5 shows ceramic feedthroughs built from composite monoliths built by depositing thin layers (slurry) of powder of both metal (for the leads) and ceramic for the insulator. Round feedthroughs were drawn, but the outer diameter and pattern of the leads can be widely varied. As each layer of insulator slurry is deposited (preferably by a screen printing method), it is dried, and then followed by a subsequent layer of metal. This structure does not require that the leads be uniform in cross section, nor that the ceramic be uniform throughout. If there is a reason for a graded ceramic and or metallization structure for EMI filtering—this invention will be capable of producing that. The examples shown have radial lead patterns—again this is arbitrary and lead patterns can vary greatly in number, pattern and density. This method of construction is different from the others, but produces structures that could be the same as those produced by other aspects of the invention that are built using metal powder. The advantage to this method is that the outer diameter can be essentially finished as produced in the unfired state, taking into account the shrinkage that occurs during densification.

51—Monolithic ceramic/metal feedthrough structure constructed by laying down layers of powder—metal and ceramic where dark central line is metal powder and white structure is ceramic powder.

52—Insulator ceramic

53—Conductive metal

54—Metal flange shown brazed to the outer diameter of 51.

55—Monolithic ceramic/metal feedthrough structure constructed by laying down layers of powder—metal and ceramic where dark central lines are metal powder and white structure is ceramic. Many leads.

56—Top and sectional views of a brazed feedthrough using 55.

57—Braze material.

58—Top and sectional view of feedthrough constructed of sintered 51, braze 57 and metal flange 54

Note that the drawings show non limiting examples. Traces could range from one to many and the pattern of traces changed to suit application. One or more traces could be patterned to ground at the flange and the shape of the monolithic ceramic composite could vary as required by design. This form of the invention has the potential to form metallization for bonding at the outer diameter of the ceramic out of the same material as the lead(s).

Figure 6:
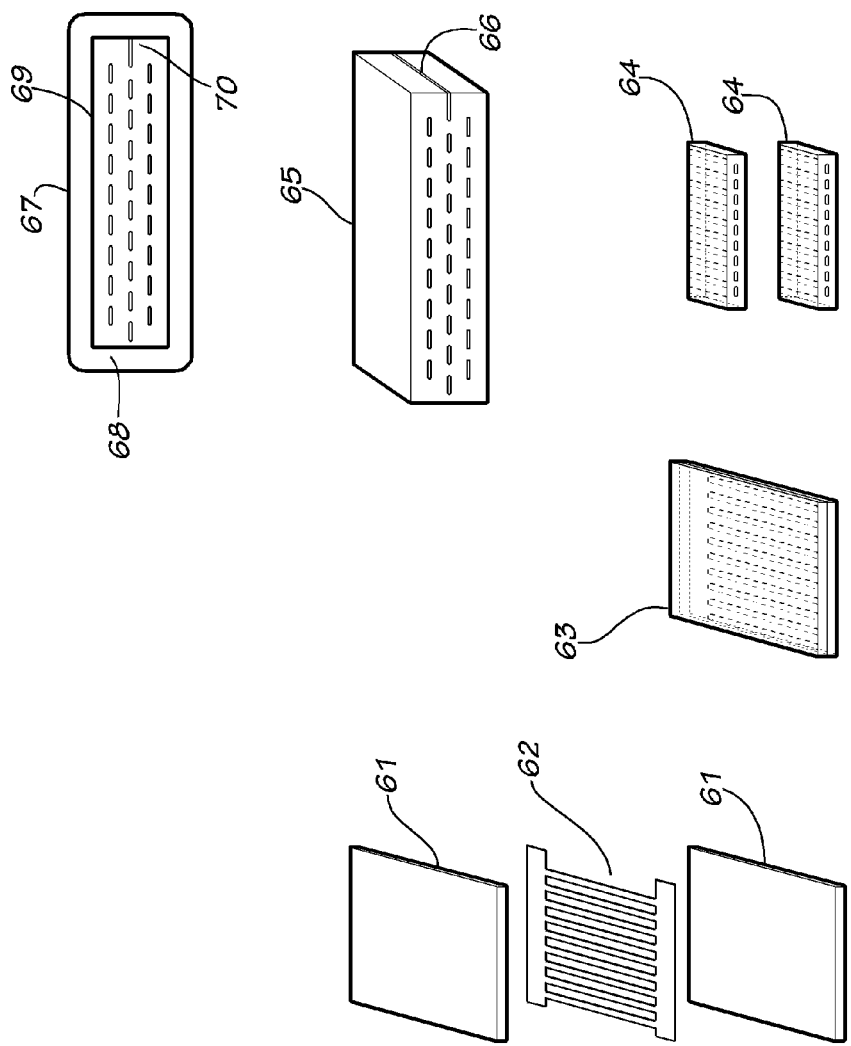
FIG. 6 is a set of views of a first exemplary feedthrough formed by laying conductive foil between layers of unpatterned insulative material.

Formed Foil Construction FIG. 6 shows a ceramic feedthrough built by layering platinum foil between layers of unpatterned (unfired) alumina substrates. As with the metallic ink versions, the cross sectional area and pattern of the lead(s) can be varied.

61—Insulator substrate—not sintered or fully densified.

62—Thin metal foil patterned to form multiple conductive paths. Ends of foil are shown connecting the conductive paths to ease assembly.

63—Assembly made of two layers of 61 sandwiching a layer of 62.

64—Sintered monolithic ceramic/metal composite feedthrough ceramics sliced from 63.

65—Sintered monolithic ceramic metal composite feedthrough made from three layers of platinum foil similar to element 62 and four layers of substrate 61.

66—Lead that is not isolated from the outer diameter of feedthrough 65

67—Brazed feedthrough utilizing feedthrough 65, titanium flange 68, braze material 69 shown only from end on view.

68—Titanium flange

69—Braze material joining titanium flange 68 to feedthrough 65.

70—Grounded lead 66 conductively bonded to titanium flange 68 with braze material 69.

Note that the drawings show non limiting examples. The number of conductive traces could range from one to many per layer and the number of layers of traces could range from one to many.

Figure 7:
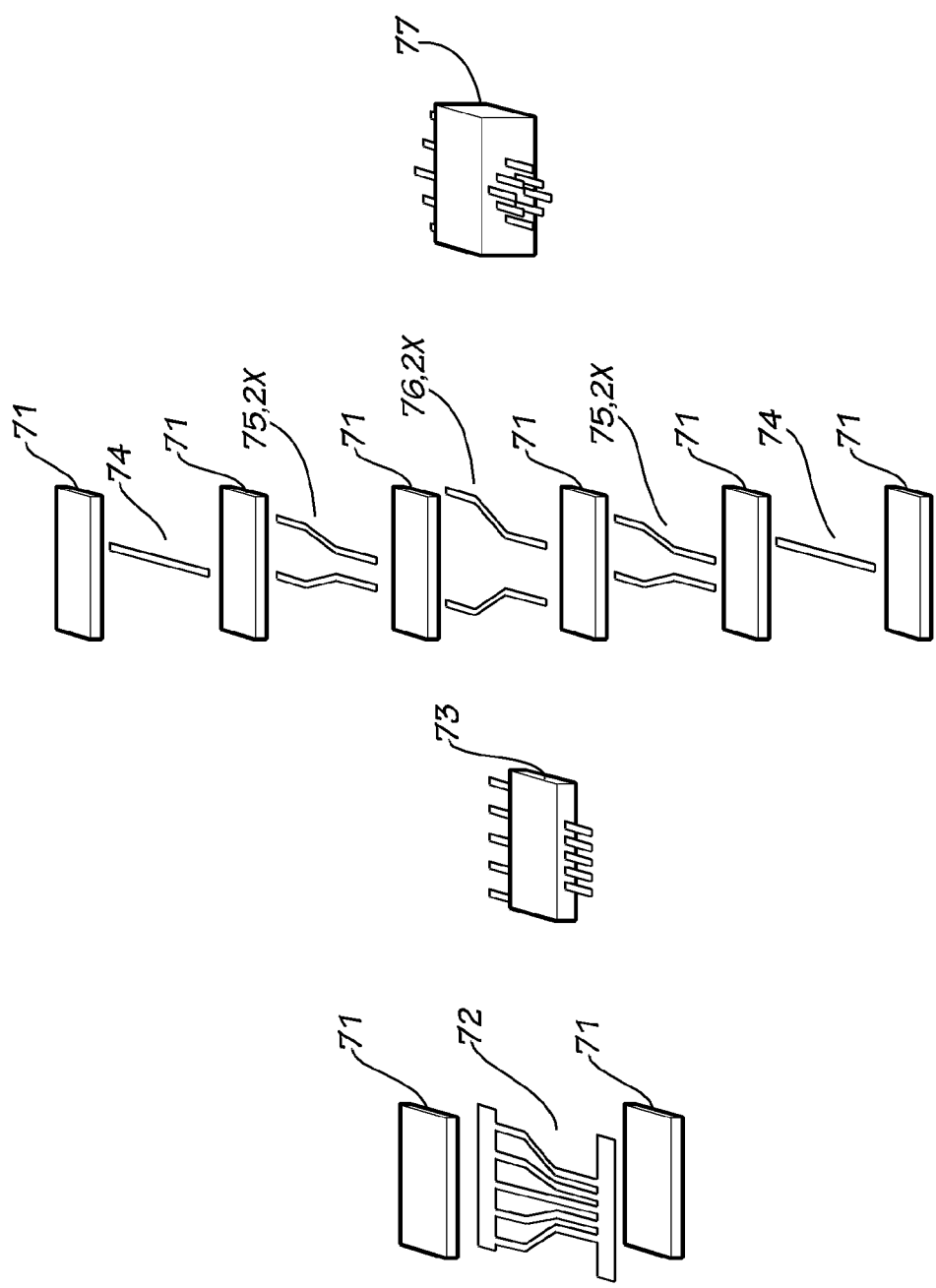
FIG. 7 is a set of views of a second exemplary feedthrough formed by laying conductive foil between layers of unpatterned insulative material.

Formed Foil Construction with Leads Extending FIG. 7 shows a ceramic feedthrough built by layering platinum foil between layers of unpatterned (unfired) alumina substrates. As with the metallic ink versions, the cross sectional area and pattern of the lead(s) can be varied.

71—Insulator substrate—not sintered or fully densified.

72—Thin metal foil patterned to form multiple conductive paths. Ends of foil are shown connecting the conductive paths to ease assembly. This connection is then severed to make isolated leads as shown in connection with element 73.

73—Assembly made of two layers of 71 sandwiching a layer of 72.

74—Thin metal foil lead

75—Thin metal foil lead.

76—Thin metal foil lead.

77—Assembly made of components 71 through 76 shown in end on view.

Note that the drawings show non limiting examples. The number of conductive leads could range from one to many per layer and the number of layers of leads could range from one to many. Leads can be essentially straight through the ceramic or bent to form an interposer as drawn.

Non-limiting, exemplary process steps for making a product consistent with FIG. 7 may include: (1) 95% substrates are initially pressed at 2000 psi; (2) 99+% platinum frame is placed between two substrates; (3) substrates with frame are then bonded together at 10000 psi; and (4) the assembly is fired at 1650 deg. C. for two hours. The foregoing is provided for purposes of illustrating, explaining, and describing embodiments of the present invention. Modifications and adaptations to these embodiments will be apparent to those skilled in the art and may be made without departing from the scope or spirit of the invention.

What is claimed is:

1. An implantable biocompatible hermetic feedthrough comprising:

a first ceramic insulative biocompatible layer having at least one bonding surface;

a second ceramic insulative biocompatible layer bonded to the first insulative layer at the bonding surface; and one or more biocompatible metal conductors compacted between the first and second insulative ceramic layers along at least a portion of the bonding surface, said bonding surface having a planar portion and the conductors disposed parallel to the planar portion such that the one or more conductors extend along the bonding surface wherein the one or more conductors and first and second insulative layers form a co-fired monolithic ceramic-to-metal composite structure after being fired together with the first and second insulative layers hermetically bonded at the bonding surface such that the one or more biocompatible conductors are exposed at both ends of the co-fired monolithic ceramic-to-metal composite structure.

2. The feedthrough of claim 1 wherein the conductor is formed of material selected from the group consisting of platinum, palladium, gold, niobium, tantalum, and alloys of any of the foregoing.

3. The feedthrough of claim 1 wherein at least one of the first or second insulative layers is formed of material selected from the group consisting of alumina, titania, zirconia, and alloys containing any of the foregoing.

4. The feedthrough of claim 1, wherein there are more than one conductors electrically isolated from each other by the insulative layers and having center-to-center spacing as low as 0.0005 inches.

5. A method of forming an implantable biocompatible hermetic feedthrough comprising:
providing a first ceramic insulative biocompatible layer with at least one bonding surface;
providing a second ceramic insulative biocompatible layer;
disposing one or more biocompatible metal conductors between the first and second ceramic insulative layers along at least a portion of the bonding surface and parallel to a planar portion of the bonding surface;
compressing the ceramic insulative biocompatible layers to facilitate alignment and bonding of the ceramic insulative layers around the biocompatible conductors;
hermetically bonding the first and second ceramic insulative layer at the bonding surface;
machining the feedthrough from the bonded insulative layers such that the one or more conductors are exposed at opposite ends of the feedthrough; and
firing the bonded first and second layers, before or after machining the feedthrough, to form a co-fired monolithic ceramic-to-metal structure.

6. The method of claim 5 wherein disposing further comprises depositing conductive material into at least one void defined by at least one insulative layer.

7. The method of claim 6 further comprising forming each of the first and second layers of insulative material as a slurry and then drying the slurry.

8. The method of claim 5 further comprising forming the one or more conductors from material selected from the group consisting of platinum, palladium, gold, niobium, tantalum, and alloys of any of the foregoing.

9. The method of claim 5 further comprising forming at least one of the first or second insulative layers from material selected from the group consisting of alumina, titania, zirconia, and alloys containing any of the foregoing.

10. The method of claim 5 further comprising defining an external surface of the freedthrough at at least one of the first and second insulative layers and forming each of the first and second insulative layers of different chemical composition than the other.

11. The feedthrough of claim 1 wherein the conductor is in the form of ink, foil, or wire.

12. The feedthrough of claim 1 wherein the conductor is vapor-deposited onto at least one of the first and second insulative layers.

13. The feedthrough of claim 1 further comprising a co-fired body comprising the bonded insulative layers mounted in a structure such that portions of the conductors lying between said bonded insulative layers extend through the structure whereby first terminal portions and second terminal portions of the conductors are exposed on different sides of the structure.

14. The feedthrough of claim 13 wherein the structure is a flange for mounting the feedthrough in a further structure.

15. The feedthrough of claim 13 wherein the terminal portions are exposed ends of the conductors.

16. The feedthrough of claim 13 wherein the conductors extend over an exposed surface of at least one of said bonded layers of insulative material to form the terminal portions.

17. The method of claim 5, wherein machining further comprises machining the bonded insulative layers to form a plurality of individually separated feedthroughs.

18. The method of claim 5, wherein machining further comprises machining the bonded insulative layers perpendicular to the planar portion to form a plurality of individually separated feedthroughs.

19. The method of claim 5, wherein bonding comprises applying pressure to the first and second insulative layers.

20. The method of claim 6, wherein disposes further comprises depositing with a pattern between the first and second insulative layers.

21. The method of claim 5, further comprising forming at least one of the first and second insulative layers as a tape.

22. The method of claim 5, further comprising alternatively layering ceramic powder and conductor, wherein said ceramic powder forms the first and second insulative layers.

23. The method of claim 6, wherein disposing further comprises forming the one or more conductors from ink, foil, or wire or powder or vapor deposited onto at least one of the first and second insulative layers.

24. The method of claim 23, wherein the one or more conductors are formed of foil and further comprising folding the foil over the ends of the feedthrough.

25. The method of claim 5, further comprising stacking multiple layers of conductors sandwiched between the first and second insulative layers.

26. The feedthrough of claim 1, further comprising a multilayer stack of conductors sandwiched between the first and second insulative layers.

27. The feedthrough of claim 1, wherein there are more than one conductors electrically isolated from each other by the insulative layers and having center-to-center spacing of as small as 0.0005 inches.

28. A feedthrough formed by the method of claim 17.

29. A feedthrough formed by the method of claim 18.

* * * * *